US006444202B1

(12) United States Patent
Kurth et al.

(10) Patent No.: US 6,444,202 B1
(45) Date of Patent: Sep. 3, 2002

(54) PROCESSED POLYPEPTIDES WITH IL-16 ACTIVITY, PROCESSES FOR THEIR PRODUCTION AND THEIR USE

(75) Inventors: Reinhard Kurth, Neu-Isenburg; Michael Baier; Albrecht Werner, both of Frankfurt; Dorothee Ambrosius; Martin Lanzendörfer, both of München, all of (DE)

(73) Assignee: Bundesrepublic Deutschland, vertreten durch den Bundesminister fur Gesundheit, Bonn (DE)

( * ) Notice: Subject to any disclaimer, the term of this patent is extended or adjusted under 35 U.S.C. 154(b) by 0 days.

(21) Appl. No.: 09/308,246
(22) PCT Filed: Nov. 2, 1997
(86) PCT No.: PCT/EP97/06476
§ 371 (c)(1),
(2), (4) Date: May 24, 1999
(87) PCT Pub. No.: WO98/23751
PCT Pub. Date: Jun. 4, 1998

(30) Foreign Application Priority Data

Nov. 25, 1996 (DE) .......................... 196 48 715
Nov. 28, 1996 (DE) .......................... 196 49 233

(51) Int. Cl.$^7$ .................... A61K 38/20; C07H 21/04
(52) U.S. Cl. .................... 424/85.2; 435/69.1; 435/325; 435/252.3; 435/320.1; 536/23.5; 530/351
(58) Field of Search ................. 435/69.1, 325, 435/252.3, 320.1; 536/23.5; 530/351; 424/85.2

(56) References Cited

U.S. PATENT DOCUMENTS

| 4,551,433 A | 11/1985 | DeBoer ...................... 435/253 |
| 4,689,406 A | 8/1987 | Banks et al. .................. 536/27 |
| 5,807,712 A | * 9/1998 | Center et al. |

FOREIGN PATENT DOCUMENTS

| DE | 196 17 202 | 11/1997 |
| EP | 0 267 85 1 B1 | 5/1988 |
| WO | 91/11520 | 8/1992 |
| WO | 92/20702 | 11/1992 |
| WO | 92/20703 | 11/1992 |
| WO | 96/31607 | 10/1996 |
| WO | 97/23615 | 7/1997 |
| WO | 97/23616 | 7/1997 |
| WO | 94 28134 | 12/1999 |

OTHER PUBLICATIONS

Cruikshank et al., "Molecular and Functional Analysis of a Lymphocyte Chemoattractant Factor: Association of Biologic . . . ," Proceedings of the National Academy of Sciences of USA, vol. 91, May 1994, pp. 5109–5113.
Bazan et al., "Interleukin–16 of Not?" Nature, vol. 381, May 2, 1996, pp. 29/30.
Bannert et al., "Interleukin–16 or Not?", Nature, vol. 381, May 2, 1996, p. 30.
Cruikshank et al., "Lymphocyte Chemoattractant Factor Induces CD4–Dependent . . . ", Journal of Immunology, vol. 146, No. 9, May 1, 1991, pp. 2928–2934.
Baier M., et al., "Molecular Cloning Sequence, Expression, and Processing of the Interleukin 16 . . . ", Proceedings of the National Academy of Sciences, vol. 94, No. 10, May 13, 1997, pp. 5273–5277.
Amann et al., Gene, "ATG vectors' for regulated high–level expression of cloned genes in *Escherichia coli*", vol. 40 (1985) pp. 183–190.
Nature, "HIV suppression by interleukin–16", vol. 378, Dec. 7, 1995.
Beck et al., Gene, "Nucleotide sequence and genome organisation of filamentous bacteriophages f1 and fd", vol. 16 (1981) 35–58.
Brosius et al., J. Mol. Biol., "Gene Organization and Primary Structure of a Ribosomal RNA Operon from *Escherichia coli*", vol. 148 (1981) 107–127.
Cruikshank et al., The Journal of Immunology, "Lymphocyte Chemoattractant Factor Induces CD4–Dependent Intracytoplasmic Signaling in Lymphocytes", vol. 146, 2928–2934, May 9, 1991.
Davies et al., Ann. Rev. Microbiol., "Plasmid–Determined Resistance to Antimicrobial Agents", 1978, 32; pp. 469–518.
Ghrayeb et al., The Embo Journal, "Secretion cloning vectors in *Escherichia coli*", vol. 3, No. 10, pp. 2437–2442, 1984.
Goeddel et al., Nucleic Acids Research, "Synthesis of human fibroblast interferon by *E.coil*" vol. 8, No. 18, 1980.
Kingsman et al., Tibtech, "The production of mammalian proteins in *Saccharomyces cerevisiae*", Feb. 1987, vol. 5.
Mach et al., Analytical Biochemistry, "Statistical Determination of the Average Values of the Extinction Coefficients of Tryptophan . . . ", 200, 74–80 (1992).
Miller et al., Bio/Technology, "Cloning and Expression of a Yeast Ubiquitin–Protein Cleaning activity in *Escherichia Coli*", vol. 7, Jul. 1989.
Nagai et al., Nature, "Generation of β–globin by sequence–specific proteolysis of a bybrid protein produced in *Escherichia Coli*", vol. 309, Jun. 28, 1984.
Oka et al., Proc. Natl. Acad. Sci., "Synthesis and secretion of human epidermal growth factor by *Escherichia Coli*", vol. 82, pp. 7212–7216, Nov. 1985.

(List continued on next page.)

Primary Examiner—Lorraine Spector
(74) Attorney, Agent, or Firm—Arent Fox Kintner Plotkin & Kahn PLLC

(57) ABSTRACT

A nucleic acid, which can be used to express a polypeptide with interleukin-16 activity in a prokaryotic or eukaryotic host cell, wherein the said nucleic acid codes for a polypeptide with the amino acid sequence SEQ ID NO:2 and/or a SEQ ID NO:2 N-terminally elongated by Ala-Ser or a form thereof which is shortened at its C-terminus by up to 8 amino acids, is suitable for producing an active IL-16 polypeptide.

9 Claims, No Drawings

OTHER PUBLICATIONS

Palva et al., Proc. Natl. Acad. Sci., "Secretion of *Escherichia coli* α–lactamase from *Bacillus subtilis* by the aid of βamylase signal sequence"., vol. 79, pp. 5582–5586, Sep. 1982.

Phillips et al., Nature, "Heat–shock proteins DnaK and GroEL facilitate export of LacZ hybrid proteins in *E. coli*", vol. 344, Apr. 26, 1990.

Powell et al., Applied and Environmental Microbiology, "A Simple and Rapid Mehtod for Genetic Transformation of Lacitc Streprococci by Electroporation", vol. 54, No. 3, Mar. 1988, pp. 655–660.

Shimatake et al., Nature, "Purified regulatory protein cll positively activates promoters for lysogenic developement", vol. 292, Jul. 9, 1981.

Studier et al., J. Mol. Biol., "Use of Bacteriophage T7 RNA Polymerase to Direct Selective High–level Expression of Cloned Genes", (1986) 189, 113–130.

Yansura, Methods in Enzymology, Expression as trpE Fusion.

* cited by examiner

PROCESSED POLYPEPTIDES WITH IL-16 ACTIVITY, PROCESSES FOR THEIR PRODUCTION AND THEIR USE

The invention concerns polypeptides with IL-16 activity, processes for their production and their use. The invention describes processed IL-16 with a high activity.

IL-16 (interleukin-16) is a lymphokine which is also referred to as lymphocyte chemoattracting factor (LCF) or immunodeficiency virus suppressing lymphokine (ISL). IL-16 and its properties are described in WO 94/28134 and in WO 96/31607 and by Cruikshank, W. W., et al., Proc. Natl. Acad. Sci. USA 91 (1994) 5109–5113 and by Baier, M., et al., Nature 378 (1995) 563. The recombinant production of IL-16 is also described in these references. According to these IL-16 is a protein with a molecular mass of 13,385 D. Cruikshank also found that ISL elutes in a molecular sieve chromatography as a multimeric form with a molecular weight of 50–60 and 55–60 kD. The chemoattractant activity has been attributed to this multimeric form which is a cationic homotetramer (product information AMS Biotechnology Ltd., Europe, Cat. No. 11177186). A homodimeric form of IL-16 with a molecular weight of 28 kD is described by Baier. However, the chemoattractant activity described by Cruikshank et al. in J. Immunol. 146 (1991) 2928–2934 and the activity of recombinant human IL-16 described by Baier are very small.

The object of the present invention is to improve the activity of IL-16 and to provide IL-16 forms which have a low immunogenicity and are advantageously suitable for a therapeutic application.

The object of the invention is achieved by a nucleic acid which can be used to express a polypeptide with interleukin-16 activity in a prokaryotic or eukaryotic host cell wherein the said nucleic acid codes for a polypeptide having the sequence SEQ ID NO:2 which is optionally N-terminally elongated by Ala-Ser-(GCCTCT).

In a further preferred embodiment the nucleic acid codes for a polypeptide with IL-16 activity which is shortened at the C-terminus by up to 8 amino acids.

Such a nucleic acid codes for a processed polypeptide with IL-16 activity with a very low antigenicity, particularly preferably natural IL-16 from primates such as human IL-16 or IL-16 of an ape species or of another mammal such as the mouse.

It has turned out that FIG. 2 of WO 94/28134 does not describe the correctly processed IL-16. The start codon "ATG" of the precursor form of the protein does not begin with nucleotide 783 but rather with nucleotide 54 or 174. This reading frame results when an A is inserted after nucleotide 156, a C is inserted after nucleotide 398 and a G is inserted after nucleotide 780. The sequence also shows further differences to FIG. 2 of WO 94/28134. These are for example nucleotide substitutions (313 G into A, 717 C into A). IL-16 is processed during the expression in eukaryotic cells. In this way a polypeptide according to SEQ ID NO:2 is formed and/or a polypeptide with a sequence which is N-terminally elongated by Ala-Ser in comparison to SEQ ID NO:2. Knowledge of the processed IL-16 enables the production of IL-16 and derivatives with high activity and low immunogenicity.

The sequence of IL-16 can differ to a certain extent from protein sequences coded by such DNA sequences. Such sequence variations may be amino acid substitutions, deletions or additions. However, the amino acid sequence of IL-16 is preferably at least 75% and particularly preferably at least 90% identical to the amino acid sequence of SEQ ID NO:2. Variants of parts of the amino and of the nucleic acid sequences SEQ ID NO:1/SEQ ID NO:2 are for example described in WO 96/31607 and the International Patent Applications PCT/EP96/05662 and PCT/EP96/05661. However, it is essential that the polypeptides have the N-terminus defined according to the invention. Thus proteins are preferred in which the first three to ten amino acids at the N-terminus are unchanged and therefore begin N-terminally with the amino acid sequences SEQ ID NO:7 to 10 or with analogous sequences which are N-terminally elongated by Ala-Ser. Proteins are also preferred which are shortened by up to 8 amino acids at the C-terminus.

Nucleic acids within the sense of the invention are understood for example as DNA, RNA and nucleic acid derivatives and analogues. Preferred nucleic acid analogues are those compounds in which the sugar phosphate backbone is replaced by other units such as e.g. amino acids. Such compounds are referred to as PNA and are described in WO 92/20702. Since PNA-DNA bonds are for example stronger than DNA-DNA bonds, the stringent conditions described below are not applicable to PNA-DNA hybridization. However, suitable hybridization conditions are described in WO 92/20703.

The term "EL-16" is understood within the sense of the invention as a polypeptide with the activity of IL-16. IL-16 preferably exhibits the stated action in the test procedure described in WO 96/31607 or stimulates cell division according to WO 94/28134.

IL-16 binds to CD4$^+$lymphocytes and can suppress the replication of viruses such as for example HIV-1, HIV-2 and SIV. The function of IL-16 is not limited by its presentation in the MHC complex.

In particular IL-16 exhibits one or several of the following properties:

binding to T cells via the CD4 receptor, stimulation of the expression of the IL-2 receptor and/or HLA-DR antigen on CD4$^+$ lymphocytes, stimulation of the proliferation of T helper cells in the presence of IL-2, suppression of the proliferation of T helper cells stimulated with anti-CD3 antibodies, suppression of the replication of viruses, preferably of HIV-1, HIV-2 or SIV.

Nucleic acids are preferred which hybridize under stringent conditions with nucleic acids which are complementary to nucleic acids of sequence SEQ ID NO:1 and code for a polypeptide of sequence SEQ ID NO:2 which is optionally N-terminally elongated by Ala-Ser-(GCCTCT). The term "hybridize under stringent conditions" means that two nucleic acid fragments hybridize with one another under standardized hybridization conditions as described for example in Sambrook et al., "Expression of cloned genes in *E. coli*" in Molecular Cloning: A laboratory manual (1989), Cold Spring Harbor Laboratory Press, New York, USA. Such conditions are for example hybridization in 6.0×SSC at about 45° C. followed by a washing step with 2×SSC at 50° C. In order to select the stringency the salt concentration in the washing step can for example be chosen between 2.0× SSC at 50° C. for low stringency and 0.2×SSC at 50° C. for high stringency. In addition the temperature of the washing step can be varied between room temperature, ca. 22° C., for low stringency and 65° C. for high stringency.

IL-16 is preferably produced recombinantly in prokaryotic or eukaryotic host cells. Such production processes are described for example in WO 94/28134 and WO 96/31607 which are also for this purpose a subject matter of the disclosure of the present invention. However, in order to obtain the forms according to the invention of IL-16 by recombinant production in a defined and reproducible manner, additional measures have to be taken beyond the processes for recombinant production familiar to a person skilled in the art.

Recombinant IL-16 can be produced by methods familiar to a person skilled in the art as a heterologous expression or homologous expression (after homologous recombination of the IL-16 nucleic acid into the genome of the host organism). For this a DNA is firstly produced which is able to produce a protein which has the activity of IL-16. The DNA is cloned into a vector which can be transferred into a host cell and can be replicated there. Such a vector contains regulatory elements in addition to the IL-16 sequence which are necessary for the expression of the DNA sequence. This vector which contains the IL-16 sequence and the regulatory elements is transferred into a vector which is able to express the DNA of IL-16. The host cell is cultured under conditions which are suitable for the amplification of the vector and IL-16 is isolated. In this process suitable measures ensure that the protein can adopt an active tertiary structure in which it exhibits IL-16 properties.

The nucleic acid sequence of the protein can also be modified. Such modifications are for example:

- modification of the nucleic acid in order to introduce various recognition sequences of restriction enzymes to facilitate the steps of ligation, cloning and mutagenesis
- modification of the nucleic acid to incorporate preferred codons for the host cell
- extension of the nucleic acid by additional operator elements in order to optimize expression in the host cell.

The protein is preferably expressed in microorganisms in particular in prokaryotes and in this case in *E. coli*. The expression in prokaryotes yields an unglycosylated polypeptide.

The expression vectors must contain a promoter which allows expression of the protein in the host organism. Such promoters are known to a person skilled in the art and are for example the lac promoter (Chang et al., Nature 198 (1977) 1056), trp promoter (Goeddel et al., Nuc. Acids Res. 8 (1980) 4057), $\lambda_{PL}$ promoter (Shimatake et al., Nature 292 (1981) 128) and T5 promoter (U.S. Pat. No. 4,689,406). Synthetic promoters such as for example the tac promoter (U.S. Pat. No. 4,551,433) are also suitable. Coupled promoter systems are equally suitable such as for example the T7-RNA polymerase/promoter system (Studier et al., J. Mol. Biol. 189 (1986) 113). Hybrid promoters composed of a bacteriophage promoter and the operator region of the microorganism (EP-A 0 267 851) are also suitable. An effective ribosome binding site is necessary in addition to the promoter. In the case of *E. coli* this ribosome binding site is referred to as the Shine-Dalgarno (SD) sequence (Sambrook et al., "Expression of cloned genes in *E. coli*" in Molecular Cloning: A laboratory manual (1989) Cold Spring Harbor Laboratory Press, New York, USA).

In order to improve expression it is possible to express the protein as a fusion protein. In this case a DNA sequence which codes for the N-terminal part of an endogenous bacterial protein or another stable protein is usually fused to the 5' end of the sequence coding for IL-16. Examples of this are for example lacZ (Phillips and Silhavy, Nature 344 (1990) 882–884), trpE (Yansura, Meth. Enzymol. 185 (1990) 161–166).

After expression of the vector which is preferably a biologically functional plasmid or a viral vector, the fusion proteins are preferably cleaved with enzymes (e.g. enterokinase or factor Xa) (Nagai et al., Nature 309 (1984) 810). Further examples of cleavage sites are the IgA protease cleavage site (WO 91/11520, EP-A 0 495 398) and the ubiquitin cleavage site (Miller et al., Bio/Technology 7 (1989) 698).

The proteins expressed in this manner in bacteria are obtained in the usual manner by disrupting the bacteria and isolating the protein.

In a further embodiment it is possible to secrete the proteins from the microorganisms as active proteins. For this a fusion product is preferably used which is composed of the signal sequence that is suitable for secretion of proteins in the host organisms used and of the nucleic acid that codes for the protein. In this case the protein is either secreted into the medium (in gram-positive bacteria) or into the periplasmatic space (in gram-negative bacteria). It is expedient to insert a cleavage site between the signal sequence and the sequence coding for IL-16 which allows cleavage of the protein either during processing or in an additional step. Such signal sequences are derived for example from ompA (Ghrayeb et al., EMBO J. 3 (1984) 2437), phoA (Oka et al., Proc. Natl. Acad. Sci. USA 82 (1985) 7212).

The vectors additionally contain terminators. Terminators are DNA sequences that signal the end of a transcription process. They are usually characterized by two structural features: a reversely repetitive G/C-rich region which can form a double helix intramolecularly as well as a number of U (or T) residues. Examples are the main terminator in the DNA of the phages fd (Beck and Zink, Gene 16 (1981) 35–38) and rrnB (Brosius et al., J. Mol. Biol. 148 (1981) 107–127).

In addition the expression vectors usually contain a selectable marker in order to select transformed cells. Such selectable markers are for example the resistance genes for ampicillin, choramphenicol, erythromycin, kanamycin, neomycin and tetracyclin (Davies et al., Ann. Rev. Microbiol. 32 (1978) 469). Selectable markers which are equally suitable are the genes for essential substances for the biosynthesis of substances necessary for the cell such as e.g. histidine, tryptophan and leucine.

Numerous suitable bacterial vectors are known. Vectors have for example been described for the following bacteria: Bacillus subtilis (Palva et al., Proc. Natl. Acad. Sci. USA 79 (1982) 5582), *E. coli* (Aman et al., Gene 40 (1985) 183; Studier et al., J. Mol. Biol. 189 (1986) 113), Streptococcus cremoris (Powell et al., Appl. Environ. Microbiol. 54 (1988) 655), Streptococcus lividans and Streptomyces lividans (U.S. Pat. No. 4,747,056).

Further genetic engineering methods for the production and expression of suitable vectors are described in J. Sambrook et al., Molecular cloning: a laboratory manual (1989), Cold Spring Harbor Laboratory Press, New York, N.Y.

In addition to prokaryotic microorganisms it is also possible to express recombinant IL-16 in eukaryotes (such as for example CHO cells, yeast or insect cells). The yeast system or insect cells are preferred as a eukaryotic expression system. Expression in yeast can be achieved by means of three types of yeast vectors: (integrating $YI_P$ (yeast integrating plasmids) vectors, replicating $YR_P$ (yeast replicon plasmids) vectors and episomal $YE_P$ (yeast episomal plasmids) vectors. More details of this are described for example in S. M. Kingsman et al. Tibtech 5 (1987) 53–57. In a particular embodiment of the invention it is possible to use a nucleic acid which represents a precursor form of the processed IL-16 polypeptide according to the invention. Such precursor forms are N-terminally elongated by further amino acids of the known IL-16 sequence in comparison with SEQ ID NO:2 and the SEQ ID NO:2 which is elongated at Ala-Ser respectively. According to the invention it is then necessary to ensure the desired processing (cleavage) in the recombinant production. This can be done for example by treating the expression product (before or after separation from the fermentation broth) with a lysate from CD8+ cells.

The invention in addition concerns a prokaryotic or eukaryotic host cell which is transformed or transfected with a nucleic acid which codes for an IL-16 polypeptide according to the invention in such a way that the host cell expresses the said polypeptide. Such a host cell usually contains a biologically functional nucleic acid vector, preferably a DNA vector, a plasmid DNA, which contains this nucleic acid.

A monomeric IL-16 polypeptide is additionally preferred which cannot be cleaved into further subunits.

It has turned out that the nucleic acid and the protein sequence of IL-16 described in WO 94/28134 do not correspond to the natural human sequences. It is merely an unnatural IL-16 analogue. However, a protein is preferably used for a therapeutic application which is either identical to the natural protein or only differs slightly from the natural protein and/or at least exhibits comparable activity and immunogenicity. The sequence of the protein is described in SEQ ID NO:2 (optionally with N-terminal elongation by Ala-Ser and/or shortening by up to 8 amino acids at the C-terminus).

The nucleic acid sequence of IL-16 can, within the scope of the invention contain deletions, mutations and additions. The monomeric form of IL-16 can be multimerized in a further embodiment. The activity of IL-16 can be increased in this manner. Such multimeric forms are preferably dimeric, tetrameric or octameric forms.

In a further embodiment the polypeptides of the invention can additionally contain a defined amount of metal ions, the number of metal ions per subunit being preferably 0.5 to 2.

Numerous metal ions are suitable as metal ions within the sense of the invention. It has turned out that alkaline earth metals as well as elements of the side groups are suitable. Alkaline earth metals, cobalt, zinc, selenium, manganese, nickel, copper, iron, magnesium, calcium, molybdenum and silver are particularly suitable. The ions may be monovalent, divalent, trivalent or tetravalent. Divalent ions are particularly preferred. The ions are preferably added as solutions of $MgCl_2$, $CaCl_2$, $MnCl_2$, $BaCl_2$, $LiCl_2$, $Sr(NO_3)_2$, $Na_2MoO_4$, $AgCl_2$.

Such multimeric forms and forms of IL-16 containing metal ions are described in the International Patent Application PCT/EP96/05661.

The polypeptide according to the invention can be produced by culturing a prokaryotic or eukaryotic host cell which has been transformed or transfected with a nucleic acid sequence as claimed in claims 1 or 2 under suitable nutrient conditions and optionally isolating the desired polypeptide. If it is intended to produce the polypeptide in vivo in the context of a gene therapy treatment, the polypeptide is of course not isolated from the cell.

A further subject matter of the invention is a pharmaceutical composition which contains a polypeptide according to the invention in an amount and/or specific activity which is sufficient for a therapeutic application as well as optionally a pharmaceutically suitable diluent, adjuvant and/or carrier.

The polypeptides according to the invention are especially suitable for treating pathological states which are caused by viral replication, in particular retroviral replication, and for immunomodulation. Such therapeutic applications are also described in the WO 96/31607. This also describes diagnostic test procedures.

The polypeptides according to the invention can be preferably used for immunosuppression. This immunosuppression is preferably achieved by an inhibition of the helper function of the $TH_0$ and/or $TH_1$ and $TH_2$ cells. Hence the polypeptides according to the invention are of therapeutic value in all diseases in which an immunodysregulatory component is postulated in the pathogenesis and in particular a hyperimmunity. Diseases which can be treated by IL-16 in cardiology/angiology are for example myocarditis, endocarditis and pericarditis, in pulmonology for example bronchitis, asthma, in haematology autoimmune neuropenias and transplant rejections, in gastroenterology chronic gastritis, in endocrinology diabetes mellitus type I, in nephrology glomerulonephritis, rheumatic diseases, diseases in ophthalmology, in neurology such as multiple sclerosis and eczemas in dermatology. The polypeptides according to the invention can be used in particular for autoimmune diseases, allergies and to avoid transplant rejections.

The invention furthermore concerns the use of the nucleic acids according to the invention within the context of gene therapy. Retroviral or non-viral vector systems are for example suitable vector systems for this.

In addition the invention concerns a polyclonal or monoclonal anti-IL-16 antibody or an immunoactive fragment thereof which binds to the first 3–20 amino acids of SEQ ID NO:2 and/or a SEQ ID NO:2 which is N-terminally elongated by Ala-Ser as well as processes for the production of such antibodies and their use for the determination of IL-16 and for determining viral infections in eukaryotic cells and in particular in mammalian cell material. Virus-activated mammalian cells, in particular T cells, can also be determined with L-16. The production of such antibodies is carried out by immunization with a polypeptide according to the invention. The production of such an antibody is carried out according to processes familiar to a person skilled in the art by immunization with an immunogen which contains the first 3–20 amino acids of SEQ ID NO:2 or a SEQ ID NO:2 N-terminally elongated by Ala-Ser as the hapten. Subsequently the antibody can be isolated from the immunized mammal in the usual way and optionally it is possible to produce a monoclonal antibody.

The following examples and publications as well as the sequence listing further elucidate the invention the protective scope of which results from the patent claims. The processes described are to be understood as examples that still describe the object of the invention even after modifications.

EXAMPLE 1

Cloning, Expression and Purification of IL-16

1.1 RNA Isolation $5 \times 10^7$ PBMC (from humans or monkeys) were cultured for 48 hours with 10 µg/ml concanavalin A and 180 U/ml IL-2. In order to prepare the RNA, the cells were washed once with PBS and subsequently lysed with 5 ml denaturation solution (RNA isolation kit, Stratagene). The lysate was kept on ice for 15 min after addition of 1 ml Na acetate, 5 ml phenol and 1 ml chloroform/isoamyl alcohol (24:1). The aqueous phase was subsequently mixed with 6 ml isopropanol in order to precipitate the RNA and stored for 2 hours at −20° C. The precipitate was finally washed once with pure ethanol and dissolved in 150 µl $H_2O$. The yield was determined photometrically and was 120 µg.

1.2 cDNA Synthesis

The mixture for the cDNA synthesis contained 10 µg RNA, 0.2 µg oligo-dT, 13 mM DTT and 5 µl bulk first strand reaction mix (first strand cDNA synthesis kit, Pharmacia) in an amount of 15 µl. The mixture was incubated for 1 hour at 37° C. and subsequently stored at −20° C. for later use.

The amplification, cloning of IL-16 cDNA and production of an expression clone is carried out as described in WO 94/28134 or WO 96/31607 taking the modified sequences into consideration.

1.3 10 l Fermentation of an *E. coli* Expression Clone for IL-16 and High Pressure Disruption Precultures are set up from stock cultures (plate smear or ampoules stored at −20° C.) which are incubated at 37° C. while shaking. The inoculation volume into the next higher dimension is 1–10 vol. % in each case. Ampicillin (50–100 mg/l) is used in the preculture and main culture to select against plasmid loss.

Enzymatically digested protein and/or yeast extract as a N- and C-source as well as glycerol and/or glucose as an additional C-source are used as nutrients. The medium is buffered to pH 7 and metal salts are added at physiologically tolerated concentrations to stabilize the fermentation process. The fermentation is carried out as a feed batch with a mixed yeast extract/C sources dosage. The fermentation temperature is 25–37° C. The dissolved partial oxygen pressure ($pO_2$) is kept approximately at <20% by means of the aeration rate, r.p.m. regulation and dosage rate. The growth is determined by determining the optical density (OD) at 528 nm. The expression of IL-16 is induced by means of IPTG. After a fermentation period of 10 to 20 hours the biomass is harvested by centrifugation at OD standstill.

The biomass is taken up in 50 mM sodium phosphate, 5 mM EDTA, 100 mM sodium chloride, pH 7 and is disrupted at 1000 bar by means of a continuous high pressure press. The suspension obtained in this manner is centrifuged again and the supernatant which contains the dissolved IL-16 is processed further.

1.4 Purification of Recombinant Human IL-16

550 ml lysis supernatant in 50 mM sodium phosphate, 5 mM EDTA, 100 mM NaCl, pH 7.2 was admixed with 55 ml 5 M NaCl, 60 mM $MgCl_2$, pH 8.0, stirred for 30 minutes and subsequently centrifuged for 30 minutes at 20,000 g. 400 ml of the supernatant was taken up on a nickel-chelate Sepharose column (V=60 ml; Pharmacia), which had previously been loaded with 30 μMol $NiCl_2$/ml gel and equilibrated with 50 mM sodium phosphate, 0.2 M NaCl, pH 8.0. The column was subsequently washed with 300 ml 50 mM sodium phosphate, 0.5 M NaCl, pH 7.0 and the IL-16 fusion protein was then eluted with a gradient of 0 M to 300 mM imidazole, pH 7.0 in 50 mM sodium phosphate, 0.1 M NaCl, pH 7.0 (2×0.5 l gradient volume). Fractions containing IL-16 were identified by means of SDS-PAGE, pooled and dialysed against 20 mM sodium phosphate, pH 7.0.

300 mg of the fusion protein obtained in this way was dialysed at 4° C. against 20 l 20 mM imidazole, pH 5.5 and subsequently centrifuged for 30 minutes at 20,000 g in order to remove turbidities. The supernatant of the centrifugation was subsequently adjusted to pH 8.5 with NaOH, admixed with 0.3 mg thrombin (Boehringer Mannheim GmbH, DE) and incubated for 4 hours at 37° C. Subsequently the cleavage mixture was adjusted to pH 6.5 with HCl and the conductivity was set to 1.7 mS by dilution with $H_2O$. The sample was applied to a Q-Sepharose FF column (45 ml; Pharmacia) which had previously been equilibrated with 20 mM imidazole, pH 6.5. IL-16 was eluted using a gradient of 0 to 0.3 M NaCl in 20 mM imidazole, pH 6.5. Fractions containing IL-16 were identified by means of SDS-PAGE and pooled. The identity of IL-16 was confirmed by means of mass analysis (molecular weight 13,566±3D) and automated N-terminal sequence analysis. The UV absorbance of IL-16 at 280 nm and a calculated molar extinction coefficient of 5540 $M^{-1}$ $cm^{-1}$ at this wavelength (Mack et al. (1992) Analyt. Biochem. 200, 74–80) were used to determine the concentration.

In order to obtain the desired N-terminus it is optionally recleaved using an aminopeptidase (e.g. α aminoacylpeptide hydrolase) or dipeptidylpeptidase (e.g. cathepsin CCATH).

The IL-16 obtained in this manner had a purity of more than 95% in SDS-PAGE under reducing conditions.

A Vydac, Protein & Peptide C18, 4×180 mm column was used to analyse purity by means of RP-HPLC. It was eluted with a linear gradient of 0% to 80% B (solvent B: 90% acetonitrile in 0.1% TFA; solvent A: 0.1% TFA in $H_2O$) within 30 minutes at a flow rate of 1 ml/min. Detection was at 220 nm.

EXAMPLE 2

Production of Shortened IL-16 Using an Enterokinase Cleavage Site 2.1 Expression Clone The amplification, cloning of IL-16 cDNA and production of an expression clone is carried out as described in WO 94/28134 or WO 96/31607 taking the modified sequences into consideration.

An oligonucleotide of sequence SEQ ID NO:3 is used as a forward primer which contains an EcoRI site, 6 His and an enterokinase cleavage site ($D_4K$):

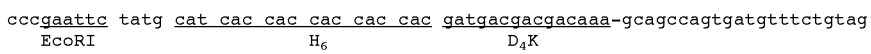

An oligonucleotide of the sequence SEQ ID NO:6 is used as a forward primer for the sequence elongated by Ala-Ser at the 5' end which also contains an EcoRI site, 6 His and an enterokinase cleavage site ($D_4K$):

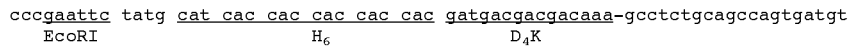

Oligonucleotide IL-16 $R_1$ (SEQ ID NO:4) IL16-$R_1$:

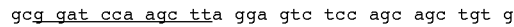

or oligonucleotide IL-16 $R_2$ (SEQ ID NO:5) IL16-$R_2$:

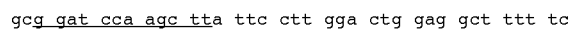

is used as the reverse primer.

The two reverse primers contain BamHI and HindIII cleavage sites for the cloning.

A sequence is obtained using IL-16 $R_1$ which codes for a protein according to SEQ ID NO:2.

A sequence is obtained using IL-16 $R_2$ which codes for an IL-16 shortened at the C-terminus by 8 amino acids. This C-terminal IL-16 is also active.

The PCR reaction, cloning and production of the expression clone (fusion protein with N-terminal poly-His part for purification) is carried out according to standard conditions:

0.2 mM dNTP mix, 1 pmol/µl each forward and reverse primer, 1× high fidelity buffer (Boehringer Mannheim GmbH, DE) 1.5 mM $MgCl_2$, 2.6 U high fidelity enzyme mix (Boehringer Mannheim GmbH, DE).

20 µl final volume instrument: Perkin Elmer GeneAmp 9600

Reaction course:

3 min 94° C., 1 min 56° C., 2 min 72° C., then 25 cycles (20 sec 94° C., 20 sec 56° C., 1 min 72° C.)

2.2 Fermentation

The fermentation is carried out analogously to example 1.3.

2.3 Purification and Cleavage 700 ml lysis supernatant in 50 mM sodium phosphate, 5 mM EDTA, 100 mM NaCl, pH 7.2 was admixed with 70 ml 5 M NaCl, 60 mM $MgCl_2$, pH 8.0, stirred for 30 min and subsequently centrifuged for 30 min at 20,000 g. The centrifuged supernatant was applied to a nickel-chelate column (V=200 ml, Pharmacia) which had previously been loaded with a $NiSO_4$ solution (c=10 mg/ml) and equilibrated with 50 mM sodium phosphate, 0.5 NaCl, pH 8.0. The column was subsequently washed with equilibration buffer until the base line (UV detection at 280 nm) was nearly reached. Afterwards the column was rinsed with 1 l 50 mM sodium phosphate, 0.5 M NaCl, pH 7.0 and with 1 l 50 mM sodium phosphate, 0.1 M NaCl, pH 7.0. The fusion protein was eluted with a gradient of 0–300 mM imidazole, pH 7.0 in 50 mM sodium phosphate, 0.1 M NaCl, pH 7.0 (2×1.6 l). Fractions containing IL-16 were identified by means of SDS-PAGE and pooled. This IL-16 pool was concentrated in a Provario (Filtron, membrane omega 5 K) to a concentration of 5 mg protein/ml and dialysed against 50 mM Tris, pH 8.0.

An equivalent of the pool containing 100 mg fusion protein was diluted to a protein concentration of c=1 mg/ml with 50 mM Tris, pH 8.0 for the enterokinase cleavage. After adding 33 µg enterokinase (Boehringer Mannheim GmbH; 1:3000 w/w) the cleavage preparation was incubated overnight (14 h) at 37° C. Subsequently the pH value was adjusted to pH 6.5 with HCl.

Uncleaved IL-16 was removed by stirring in 20 ml nickel-chelate sepharose (prepared as above; binding time 2 h) and subsequent centrifugation (10,000 g) or filtering the supernatant over a nutsch filter. The identity of the cleaved IL-16 contained in the supernatant was confirmed by N-terminal sequencing and mass analysis. The purity was checked by SDS-PAGE and RP-HPLC (Vydac, Diphenyl, 4.6×150 mm, linear gradient from 20% to 95% B within 45 minutes; solution A: 20 mM potassium phosphate in $H_2O$, pH 7.5; solution B: 100% acetonitrile).

EXAMPLE 3

Cleavage of Recombinant IL-16 with Cell Lysate 3.1 Separation of $CD8^+$ and $CD4^+$ Lymphocytes Via MACS The lymphocytes isolated from a buffy coat by means of Ficoll gradients are resuspended in 500 µl PBS-azide/1×$10^8$ cells (phosphate buffered saline without $Ca^{2+}$ and $Mg^{2+}$, 0.01% sodium azide, 5 mM EDTA, pH 7.2). After addition of 20 ml CD8 microbeads/1×$10^7$ cells to be expected (mouse anti-human CD8 antibodies, conjugated with magnetic particles, Miltenyi Biotec GmbH), they are incubated for 15 min at 4° C. 2 mg DTAF/1×$10^7$ expected cells (anti-mouse IgG FITC conjugated, Dianova Company) is added for a further 5 min at 4° C. After dilution with 25 ml PBS-azide/1% BSA it is again centrifuged (10 min, 1200 rpm, 4° C.). The supernatant is discarded, the cells are resuspended in 2 ml PBS/1% BSA and the cell suspension is applied to a column which is located in a magnetic separator (Miltenyi Biotec GmbH). The $CD8^+$ cells to which the CD8 microbeads are coupled are retained in the column, thus the flow fraction contains all lymphocytes (ca. 80% $CD4^+$ cells) except the $CD8^+$ cells. After washing the column is taken out of the holder and the $CD8^+$ cell fraction is eluted with PBS-azide/1% BSA. The flow fraction and the $CD8^+$ cell fraction are centrifuged, resuspended in cell culture medium (RPMI 1640, 20% FCS, 2 mM glutamine, 180 U/ml IL-2), the cell count is adjusted to 3×$10^6$ cells/ml and the cells are stimulated with PHA (9 mg/ml). The quality of the separation of the lymphocyte subpopulation is checked by means of FACS (requirement: >90% $CD8^+$ cells).

3.2 Production of Cell Lysate and Digestion of IL-16

1×$10^8$ $CD8^+$ lymphocytes which had been stimulated for three days with PHA and cultured for another three days without PHA but with IL-2 (180 U/ml cell culture) are lysed for 10 min on ice in 2 ml PBS which is admixed with 1% Triton X100. Then cell debris and cell nuclei are removed by ultracentrifugation (100,000× g/10 min). 45 µl of the cell lysate obtained in this manner is incubated for 16 hours at room temperature with 10 µg recombinant IL-16 which was expressed either at the amino-terminal or carboxy-terminal end in fusion with a histidine tag (HIS tag, e.g. six histidines with a cleavage site cf WO 94/28134). The proteolytic digestion is analyzed in an immunoblot. Then the fragments carrying the HIS tag are removed with the aid of a nickel agarose matrix. The processed rIL-16 peptide is purified with the aid of an antibody column. Protein G agarose to which monoclonal or polyclonal antibodies against rIL-16 are covalently bound is used as a column matrix. For covalently cross-linking the antibodies with the matrix for instance dimethylpimelimidate can be used. rIL-16 is eluted with 50 mM triethylamine pH 12. Equal volumes of 1 M Tris pH 7.0 are applied into the fraction tubes to adjust the pH. The enriched rIL-16 fraction is separated via a reversed phase column (e.g. Vydac RP4 1 mm×15 cm). The application is done in 0.5 M Tris, 25 mM triethylamine pH 7.0. IL-16 is eluted with a gradient of the buffers A: 0.1% TFA and B: 0.08% TFA 80% acetonitrile at a flow of 0.05 ml/min (elution in 20 min from 10% to 100% TFA). Last, the masses of the fragments are determined by mass spectroscopy and the size and sequence of the processed IL-16 are in this way determined. A naturally processed IL-16 fragment beginning with the N terminus set forth in SEQ ID NO: 2 and elongated by two amino acids respectively was identified in this manner.

LIST OF REFERENCES

Aman et al., Gene 40 (1985) 183
Baier, M., et al., Nature 378 (1995) 563
Beck and Zink, Gene 16 (1981) 35–58
Brosius et al., J. Mol. Biol. 148 (1981) 107–127
Chang et al., Nature 198 (1977) 1056
Cruikshank, W. W., et al., J. Immunol. 146 (1991) 2928–2934
Cruikshank, W. W., et al., Proc. Natl. Acad. Sci. USA 91 (1994) 5109–5113
Davies et al., Ann. Rev. Microbiol. 32 (1978) 469

EP-A 0 267 851
EP-A 0 495 398
Ghrayeb et al., EMBO J. 3 (1984) 2437
Goeddel et al., Nuc. Acids Res. 8 (1980) 4057
International Patent Application PCT/EP96/05661
International Patent Application PCT/EP96/05662
Kingsman, S. M., et al, Tibtech 5 (1987) 53–57
Mack et al., Analyt. Biochem. 200 (1992) 74–80
Miller et al., Bio/Technology 7 (1989) 698
Nagai et al., Nature 309 (1984) 810
Oka et al., Proc. Natl. Acad. Sci. USA 82 (1985) 7212
Palva et al., Proc. Natl. Acad. Sci. USA 79 (1982) 5582
Phillips and Silhavy, Nature 344 (1990) 882–884
Powell et al., Appl. Environ. Microbiol. 54 (1988) 655

Sambrook et al., "Expression of cloned genes in *E. coli*" in Molecular Cloning: A laboratory manual (1989), Cold Spring Harbor Laboratory Press, New York, USA
Shimatake et al., Nature 292 (1981) 128
Studier et al., J. Mol. Biol. 189 (1986) 113
U.S. Pat. No. 4,551,433
U.S. Pat. No. 4,689,406
U.S. Pat. No. 4,747,056
WO 91/11520
WO 92/20702
WO 92/20703
WO 94/28134
WO 96/31607
Yansura, Meth. Enzymol. 185 (1990) 161–166

What is claimed is:

1. An isolated nucleic acid encoding a polypeptide with interleukin 16 activity, wherein the polypeptide consists the sequence of SEQ ID NO: 2 or SEQ ID NO: 2 elongated at the N-terminal end by Ala-Ser.

2. The nucleic acid as claimed in claim 1, wherein the nucleic acid comprising the sequence of SEQ ID NO: 1 is from a primate.

3. Prokaryotic or eukaryotic host cell which is transformed or transfected with a nucleic acid as claimed in claim 1, wherein the host cell expresses the polypeptide.

4. An expression vector comprising a nucleic acid as claimed in claim 1.

5. A nucleic acid of claim 1, wherein the polypeptide consists of SEQ ID NO:2 elongated at the N-terminal end by Ala-Ser.

6. An isolated recombinant polypeptide consisting of the sequence of SEQ ID NO: 2 or SEQ ID NO:2 elongated at the N-terminal end by Ala-Ser, and obtainable from a eukaryotic or prokaryotic host cell.

7. An isolated recombinant human interleukin 16 polypeptide or an elongated precursor form thereof, consisting of the sequence of SEQ ID NO: 2 or SEQ ID NO:2 elongated at the N-terminal end by Ala-Ser, and obtainable from a eukaryotic host cell.

8. A process for production of the polypeptide of claim 6 or 7, comprising providing a prokaryotic or eukaryotic host cell which is transformed or transfected with the nucleic acid sequence of SEQ ID NO: 1;

culturing the host cell under nutrient conditions for the host cell to produce the polypeptide; and isolating the desired polypeptide produced by the cell.

9. A pharmaceutical composition suitable for immune suppression or antiviral therapy, comprising a polypeptide as claimed in claim 6 in an immunosuppressive or antiviral effective amount, and a pharmaceutically acceptable diluent, adjuvant and/or carrier.

* * * * *

SEQUENCE LISTING

```
<160> NUMBER OF SEQ ID NOS: 10

<210> SEQ ID NO 1
<211> LENGTH: 348
<212> TYPE: DNA
<213> ORGANISM: Artificial Sequence
<220> FEATURE:
<221> NAME/KEY: CDS
<222> LOCATION: (1)..(348)
<221> NAME/KEY: misc_feature
<222> LOCATION: (1)..(348)
<223> OTHER INFORMATION: Prepared in a laborato ry.

<400> SEQUENCE: 1 gca gcc agt gat gtt tct gta gaa tct aca g ca gag gcc aca gtc tgc     48
Ala Ala Ser Asp Val Ser Val Glu Ser Thr A la Glu Ala Thr Val Cys
1               5                  10                  15 acg gtg aca ctg gag aag atg tcg gca ggg c tg ggc ttc agc ctg gaa     96
Thr Val Thr Leu Glu Lys Met Ser Ala Gly L eu Gly Phe Ser Leu Glu
            20                  25                  30 gga ggg aag ggc tcc cta cac gga gac aag c ct ctc acc att aac agg    144
Gly Gly Lys Gly Ser Leu His Gly Asp Lys P ro Leu Thr Ile Asn Arg
        35                  40                  45 att ttc aaa gga gca gcc tca gaa caa agt g ag aca gtc cag cct gga    192
Ile Phe Lys Gly Ala Ala Ser Glu Gln Ser G lu Thr Val Gln Pro Gly
    50                  55                  60 gat gaa atc ttg cag ctg ggt ggc act gcc a tg cag ggc ctc aca cgg    240
Asp Glu Ile Leu Gln Leu Gly Gly Thr Ala M et Gln Gly Leu Thr Arg
65                  70                  75                  80 ttt gaa gcc tgg aac atc atc aag gca ctg c ct gat gga cct gtc acg    288
Phe Glu Ala Trp Asn Ile Ile Lys Ala Leu P ro Asp Gly Pro Val Thr
                85                  90                  95 att gtc atc agg aga aaa agc ctc cag tcc a ag gaa acc aca gct gct    336
Ile Val Ile Arg Arg Lys Ser Leu Gln Ser L ys Glu Thr Thr Ala Ala
            100                 105                 110 gga gac tcc tag                                                     348
Gly Asp Ser
        115

<210> SEQ ID NO 2
<211> LENGTH: 115
<212> TYPE: PRT
<213> ORGANISM: Artificial Sequence
<220> FEATURE:
<221> NAME/KEY: PEPTIDE
<222> LOCATION: (1)..(115)
<223> OTHER INFORMATION: Prepared in a laborato ry.
```

```
<400> SEQUENCE: 2

Ala Ala Ser Asp Val Ser Val Glu Ser Thr Ala Glu Ala Thr Val Cys
1               5                   10                  15

Thr Val Thr Leu Glu Lys Met Ser Ala Gly Leu Gly Phe Ser Leu Glu
            20                  25                  30

Gly Gly Lys Gly Ser Leu His Gly Asp Lys Pro Leu Thr Ile Asn Arg
        35                  40                  45

Ile Phe Lys Gly Ala Ala Ser Glu Gln Ser Glu Thr Val Gln Pro Gly
    50                  55                  60

Asp Glu Ile Leu Gln Leu Gly Thr Ala Met Gln Gly Leu Thr Arg
65                  70                  75                  80

Phe Glu Ala Trp Asn Ile Ile Lys Ala Leu Pro Asp Gly Pro Val Thr
                85                  90                  95

Ile Val Ile Arg Arg Lys Ser Leu Gln Ser Lys Glu Thr Thr Ala Ala
            100                 105                 110

Gly Asp Ser
        115
```

```
<210> SEQ ID NO 3
<211> LENGTH: 68
<212> TYPE: DNA
<213> ORGANISM: Artificial Sequence
<220> FEATURE:
<221> NAME/KEY: misc_feature
<222> LOCATION: (1)..(68)
<223> OTHER INFORMATION: Reverse primer IL-16-R1 prepared in a
      laboratory.

<400> SEQUENCE: 3
cccgaattct atgcatcacc accaccacca cgatgacgac gacaaagcag c cagtgatgt     60 ttctgtag                                                              68

<210> SEQ ID NO 4
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: Reverse primer IL-16-R1 prepared in a
      laboratory.

<400> SEQUENCE: 4
gcggatccaa gcttaggagt ctccagcagc tgtg                                 34

<210> SEQ ID NO 5
<211> LENGTH: 38
<212> TYPE: DNA
<213> ORGANISM: Artificial Sequence
<220> FEATURE:
<221> NAME/KEY: misc_feature
<222> LOCATION: (1)..(38)
<223> OTHER INFORMATION: Reverse primer IL-16-R2 prepared in a
      laboratory.

<400> SEQUENCE: 5
gcggatccaa gcttattcct tggactggag gcttttttc                            38

<210> SEQ ID NO 6
<211> LENGTH: 66
<212> TYPE: DNA
<213> ORGANISM: Artificial Sequence
<220> FEATURE:
```

```
<221> NAME/KEY: misc_feature
<222> LOCATION: (1)..(66)
<223> OTHER INFORMATION: Forward primer prepared in a laboratory.

<400> SEQUENCE: 6
cccgaattct atgcatcacc accaccacca cgatgacgac gacaaagcct c tgcagccag    60 tgatgt                                                                66

<210> SEQ ID NO 7
<211> LENGTH: 7
<212> TYPE: PRT
<213> ORGANISM: Artificial Sequence
<220> FEATURE:
<221> NAME/KEY: PEPTIDE
<222> LOCATION: (1)..(7)
<223> OTHER INFORMATION: Peptide prepared in a laboratory.

<400> SEQUENCE: 7

Ala Ala Ser Asp Val Ser Val
1               5

<210> SEQ ID NO 8
<211> LENGTH: 6
<212> TYPE: PRT
<213> ORGANISM: Artificial Sequence
<220> FEATURE:
<221> NAME/KEY: PEPTIDE
<222> LOCATION: (1)..(6)
<223> OTHER INFORMATION: Peptide prepared in a laboratory.

<400> SEQUENCE: 8

Ala Ala Ser Asp Val Ser
1               5

<210> SEQ ID NO 9
<211> LENGTH: 5
<212> TYPE: PRT
<213> ORGANISM: Artificial Sequence
<220> FEATURE:
<221> NAME/KEY: PEPTIDE
<222> LOCATION: (1)..(5)
<223> OTHER INFORMATION: Peptide prepared in a laboratory.

<400> SEQUENCE: 9

Ala Ala Ser Asp Val
1               5

<210> SEQ ID NO 10
<211> LENGTH: 4
<212> TYPE: PRT
<213> ORGANISM: Artificial Sequence
<220> FEATURE:
<221> NAME/KEY: PEPTIDE
<222> LOCATION: (1)..(4)
<223> OTHER INFORMATION: Peptide prepared in a laboratory.

<400> SEQUENCE: 10

Ala Ala Ser Asp
1
```